United States Patent
Vanney et al.

[11] Patent Number: 5,843,178
[45] Date of Patent: *Dec. 1, 1998

[54] SUTURE GUARD FOR ANNULOPLASTY RING

[75] Inventors: Guy P. Vanney, Blaine; Kurt D. Krueger, Stacy; Michael J. Girard, Lino Lakes, all of Minn.

[73] Assignee: St. Jude Medical, Inc., St. Paul, Minn.

[*] Notice: The term of this patent shall not extend beyond the expiration date of Pat. No. 5,571,175.

[21] Appl. No.: 666,254

[22] Filed: Jun. 20, 1996

[51] Int. Cl.⁶ .................................................. A61F 2/24
[52] U.S. Cl. ................................................................ 623/2
[58] Field of Search .................................. 623/2, 3, 900; 606/148

[56] References Cited

U.S. PATENT DOCUMENTS

| | | |
|---|---|---|
| 3,546,710 | 12/1970 | Shumakov et al. . |
| 3,574,865 | 4/1971 | Hamaker ................................. 128/303 |
| 3,625,220 | 12/1971 | Engelsher ................................. 128/335 |
| 3,691,567 | 9/1972 | Cromie ......................................... 623/2 |
| 3,996,623 | 12/1976 | Kaster . |
| 4,009,719 | 3/1977 | Kletschka et al. ....................... 128/335 |
| 4,084,268 | 4/1978 | Ionescu et al. . |
| 4,172,295 | 10/1979 | Batten . |
| 4,233,690 | 11/1980 | Akins . |
| 4,290,151 | 9/1981 | Massana . |
| 4,388,735 | 6/1983 | Ionescu et al. . |
| 4,665,906 | 5/1987 | Jervis .......................................... 128/92 |
| 4,907,590 | 3/1990 | Wang et al. .............................. 606/139 |
| 5,061,277 | 10/1991 | Carpentier et al. .......................... 623/2 |
| 5,064,431 | 11/1991 | Gilbertson et al. .......................... 623/2 |
| 5,104,407 | 4/1992 | Lam et al. .................................... 623/2 |
| 5,290,300 | 3/1994 | Cosgrove et al. ........................ 606/148 |
| 5,571,175 | 11/1996 | Vanney et al. ............................... 623/2 |

FOREIGN PATENT DOCUMENTS

| 1180087 | 10/1964 | Germany . |
|---|---|---|
| WO 89/00841 | 2/1989 | WIPO . |

*Primary Examiner*—David J. Isabella
*Attorney, Agent, or Firm*—Hallie A. Finucane, Esq.; Westman, Champlin & Kelly, P.A.

[57] ABSTRACT

An annuloplasty prosthesis ring for implantation proximate a heart valve orifice includes a core having a size and shape to generally conform to the heart valve orifice. A sheath formed about the core is adapted for receiving a suture therethrough to attach the annuloplasty ring to the heart valve orifice. The suture is knotted on a knot surface of the sheath to form a suture knot thereon. A moveable suture guard is provided which is moveable between an open position in which the knot surface and suture knot are exposed and a closed position in which the knot surface and the suture knot carried on the knot surface are covered.

23 Claims, 17 Drawing Sheets

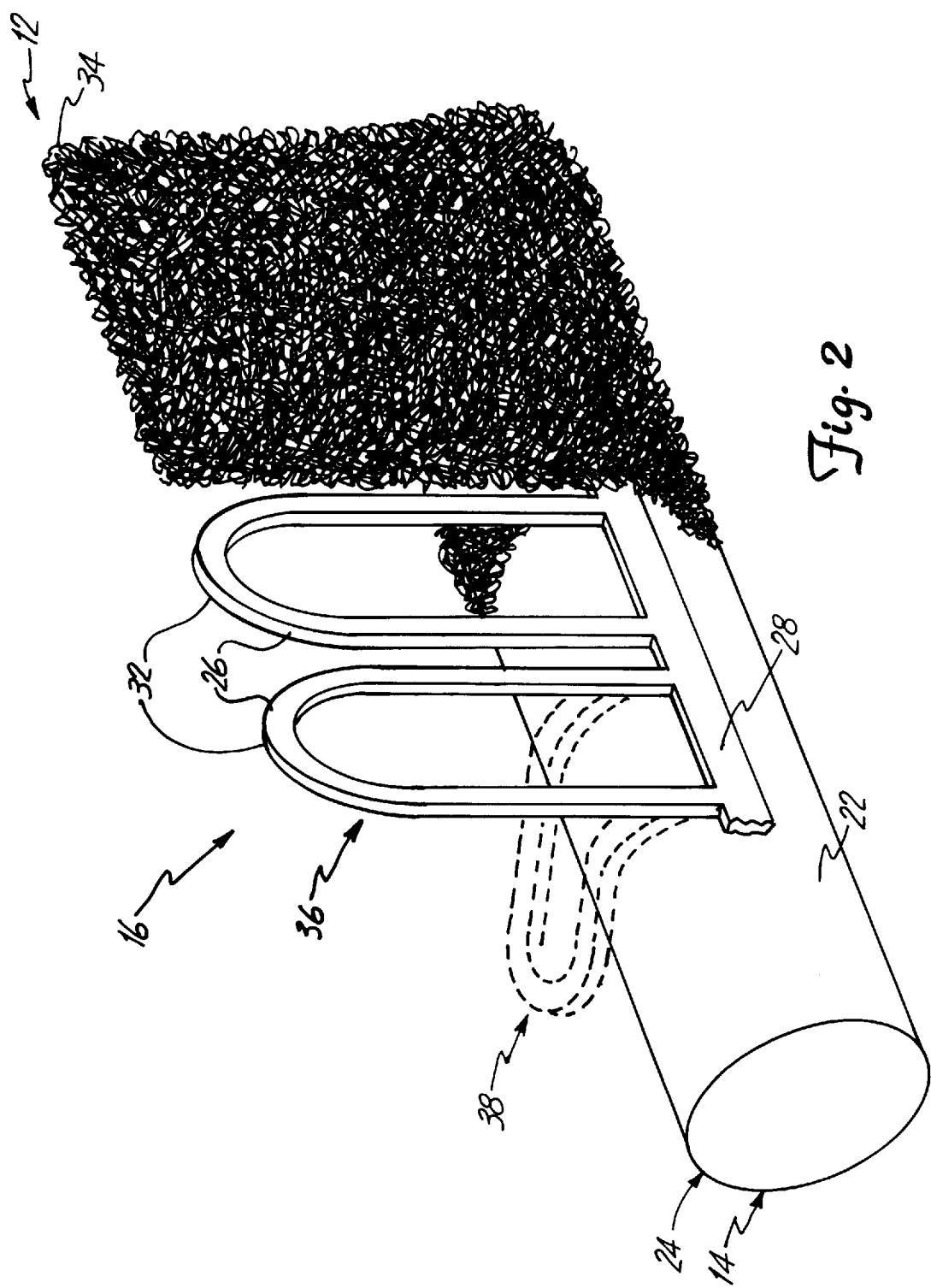

SUTURE GUARD FOR ANNULOPLASTY RING

FIELD OF THE INVENTION

The present invention relates to valve repair devices, such as annuloplasty rings. More specifically, the present invention relates to a shield or guard for covering a suture knot or other attachment mechanism used to attach an annuloplasty ring to a patient.

BACKGROUND OF THE INVENTION

Human heart valves comprise leaflets or cusps that open and close to control the flow of blood to a particular region of the heart. The mitral and tricuspid valves are located in the atrioventricular opening of the heart and function to prevent backflow of blood from the ventricle into the atrium when the ventricle contracts. The aortic valve is located between the left ventricle and the ascending aorta and functions to prevent backflow of blood into the left ventricle.

The mitral valve is located in the left atrioventricular opening of the heart. It includes two leaflets or cusps and is encircled by a dense fibrous ring known as the annulus. The anterior leaflet is located next to the aortic valve and is also known as the anterior leaflet. The posterior leaflet has a wider attachment to the annulus and is also known as the posterior leaflet. The leaflets are held in place by chordae tendineae and papillary muscles. The commissure is the point at which the annular attachment of the leaflets meet and fuse. Coaptation refers to valve closure and the meeting of the free edges of the leaflets.

The tricuspid valve is located in the right atrioventricular opening and comprises three leaflets, sometimes referred to as the anterior, posterior and septal cusps (leaflets). These leaflets are generally triangular in shape and, like the mitral valve leaflets, are attached to a fibrous ring, or annulus.

The aortic valve is composed of three segments, each of which is termed a semilunar cusp. The valve is closed during ventricular diastole and is open during systole.

One common defect leading to mitral dysfunction is excessive dilation or elongation of the posterior two-thirds of the annulus, the section corresponding to the posterior leaflet. The anterior section of the annulus is anchored to the aortic root and is therefore not as subject to elongation. However, not infrequently in cases of mitral valve dysfunction, the anterior leaflet is displaced away from the center of the valve and is slightly thickened and shortened. Thus, in repairing a mitral valve, it is sometimes necessary to reduce the annulus to its physiological dimensions by repairing the dilated portion of the valve, to ensure coaptation. It may also be necessary to restore the commissure to its normal curvature and to reposition and reshape the anterior leaflet. Similar concepts apply to correction of tricuspid valve defects.

Mitral valve repair has been performed successfully since the late 1950's. Its appeal with cardiac surgeons, however, was not immediate. Only in more recent years, as surgeons have had appropriate devices to use and have increasingly realized the advantages of repair, has the proportion of mitral valve repair increased. The clinical advantages of mitral valve repair as compared to replacement are attributed to better left ventricular function and the lack of need for long-term anticoagulation therapy. Better left ventricular function has led to a lower incidence of mitral valve stenosis and regurgitation for repair as compared to replacement procedures. The incidences of thromboembolism, hemorrhagic complications and infective endocarditis have been shown to be lower after mitral valve repair than after replacement. Actuarial survival after repair is also greater than that after valve replacement. Akins et al., *Ann. Thora. Surgery* 58: 668–76 (1994).

Annuloplasty, or annulus repair, has become an intermediate measure between non-invasive management of valvular heart disease and replacement of an entire heart valve with a prosthetic implant. Annuloplasty prostheses, for example ring-shaped devices, are used in the procedures and represent the standard method of repair. As clinical results increasingly show the annuloplasty prostheses better preserve left ventricular function, surgeons have become more enthusiastic about annuloplasty repair over valve replacement whenever feasible.

Annuloplasty prostheses differ from prosthetic heart valves in that the prostheses are designed to support diseased or damaged natural heart valves rather than replace them. An annuloplasty prosthesis is a device implanted around or in association with the mitral, tricuspid or aortic valve for reconstructive repair of valvular insufficiency. The indications for repair using annuloplasty prostheses include correction of annular dilatation, increases in leaflet coaptation, reinforcement of annular suture lines and prevention of future dilatation.

Annuloplasty prostheses consist of three types: rigid, semi-flexible and flexible. Currently available rigid or flexible prostheses may be entirely composed of a biocompatible fabric (classified as flexible) such as polyester. Alternatively, a prosthesis may constitute a multiple component system composed of a more rigid core such as titanium, polyethylene or silicone, which is then covered by a fabric (classified as rigid or flexible depending on the core material). Some of the prostheses are made radiopaque through use of metal or by impregnating polymers with barium sulfate ($BaSO_4$).

The Carpentier-Edwards® ring (see, e.g. U.S. Pat. No. 5,061,277) is classified as rigid. This prosthesis is kidney shaped with one long curved segment corresponding to the posterior annulus; the ring is open in the portion corresponding to the anterior leaflet. It is constructed of a titanium alloy core with a sewing ring margin that consists of silicone rubber covered with polyester knit fabric. The Medtronic-Duran ring (Duran et al., *Circulation* (Suppl. I) 78:91–96 (1989)) is classified as flexible and, like the Carpentier ring, is not adjustable after implantation. It is constructed of a radiopaque core of silicone elastomer impregnated with $BaSO_4$, and covered by polyester. It is claimed that this prosthesis can adapt to change in the mitral annulus, permitting optimal hemodynamics in diastole while maintaining coaptation and valve integrity in systole. The Puig-Massana Ring (see, e.g. U.S. Pat. No. 4,290,151) is a flexible and adjustable prosthesis that is also constructed of a core of silicone elastomer impregnated with $BaSO_4$. The adjustability feature is not fully functional since the ring slips under the suture line resulting in equalization of tension around the entire ring. The Carpentier-Edwards Physio™ Annuloplasty Ring (see, e.g., U.S. Pat. No. 5,104,407) and SJM® Seguin Annuloplasty Ring (see, e.g. French Patent No. 2 708 458) are semi-rigid prosthesis rings that combine support for valve repair, yet have flexible properties allowing dynamic movement throughout the cardiac cycle. Other prostheses include partial rings (e.g., Cosgrove-Edwards™, U.S. Pat. No. 5,290,300) which are constructed of polyester and are intended to be used only in the posterior mitral annular segment.

Suturing techniques for annuloplasty prostheses may vary depending on the design or the physician's preference. The suture may be placed around the prosthesis or passed through a portion of the prosthesis. Surgeons generally use either interrupted single or mattress sutures, or a continuous running suture similar to that used in prosthetic valve replacement. In these suturing techniques, a knot must be formed in the suture. Typically, a large knot is formed by the surgeon resulting from a number of knots tied one upon the other to prevent the suture from becoming unknotted. However, this provides a large knotted tail which extends from the surface of the annuloplasty prosthesis and is exposed to blood flow which may lead to thromboembolic events.

SUMMARY OF THE INVENTION

The present invention provides a shield or guard which covers the suture knots used to suture a valve repair device, such as an annuloplasty prosthesis ring to the patient's natural heart valve annulus. The annuloplasty ring includes a core having a size and shape to generally conform to the heart valve annulus. A sheath is formed about the core and is adapted for receiving a suture therethrough to attach the core to the heart valve annulus. The suture is knotted on a knot surface of the sheath to form a suture knot thereon. In various embodiments of the present invention, the core is rigid, semi-rigid or flexible and may receive the suture therethrough. A suture guard is provided which selectively covers the suture knot. The suture guard is moveable between an open position, in which the knot surface and the suture knot are exposed, and a closed position, in which the knot surface and the suture knot carried on the knot surface are covered. In some embodiments, the suture guard is attached to the sheath and/or core, when the suture guard is in the open position. In other embodiments, the suture guard is a separate piece which attaches to the sheath and covers the suture knot.

BRIEF DESCRIPTION OF THE DRAWINGS

FIG. 2 is a cut-away cross sectional perspective view of the ring prosthesis of FIG. 1A.

DETAILED DESCRIPTION OF THE PREFERRED EMBODIMENTS

Figure 1A:
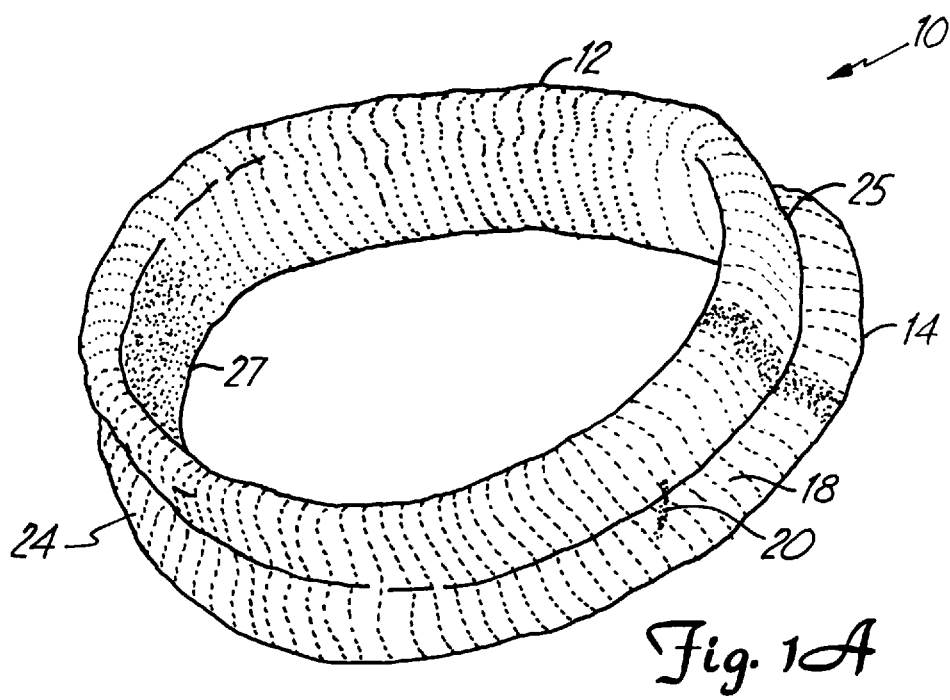
FIG. 1A is a perspective view of an annuloplasty ring prosthesis including a suture guard in accordance with one embodiment of the present invention.

FIG. 1A is a perspective view of valve repair device, such as an annuloplasty ring prosthesis 10 in accordance with one embodiment of the present invention and includes suture guard 12. Ring 10 includes core 14 which may be shaped generally like a "D" for mitral implantation. Ring 10 may also be a generally round shape for aortic implantation, or other shapes which conform to the anatomy of the heart valve. Suture guard 12 couples to the inner radius of core 14. Suture guard 12 and core 14 are covered by a sheath formed of a flexible material. For example, the sheath may be formed of a fabric such as polyester or PTFE. Suture guard 12 is attached to inner perimeter 22 of core 14 at attachment region 25. As used herein, the core may be a flexible or rigid material that provides structural benefit or acts as a space occupying region of the ring. The sheath material or other material may serve as the "core" of the annuloplasty ring prosthesis. Typically, the core is used for suture attachment; however, this is not required for the present invention which is intended to be applicable to any annuloplasty ring prosthesis. The ring may or may not have a separate core as desired.

Figure 1B:
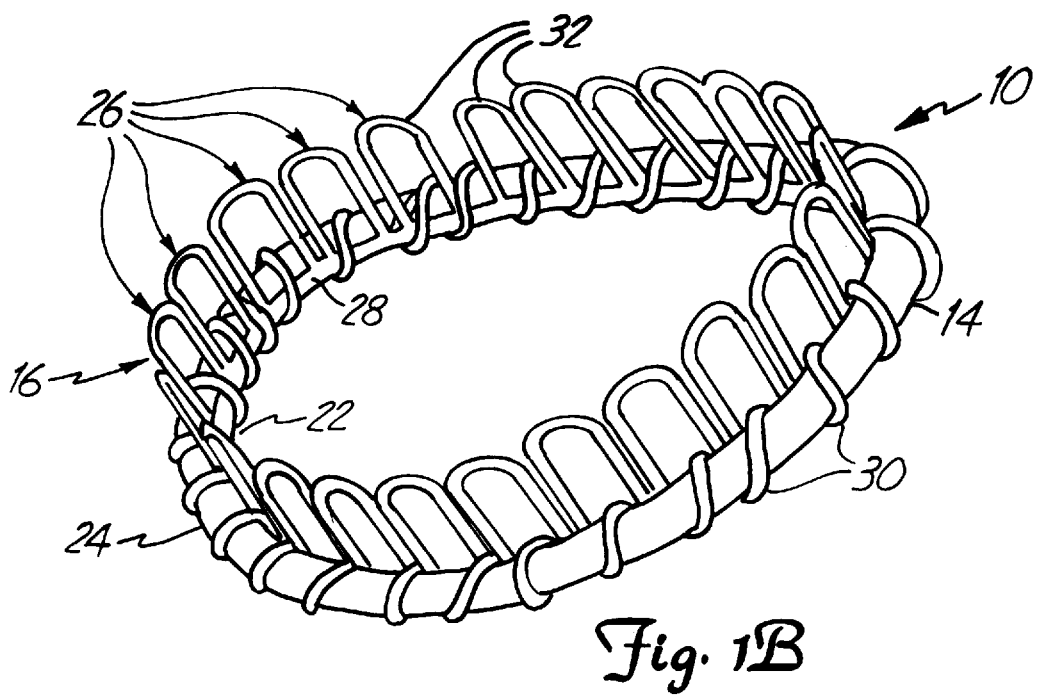
FIG. 1B is a perspective view of the ring prosthesis of FIG. 1A with sheath material removed.

FIG. 1B is a perspective view of annuloplasty ring prosthesis 10 with the sheath removed such that core 14 and bendable elements 16 are shown. Bendable elements 16 extend within the sheath and form the suture guard 12 shown in FIG. 1A. Core 14 provides suture knot surface 18 formed thereon for carrying a suture knot 20, for example. Core 14 includes an inner perimeter 22 and an outer perimeter 24.

Bendable elements 16 include a plurality of pliable loops 26 carried on support element 28. Support element 28 is secured to core 14 by coupling member 30 which may comprise, for example, an elongated suture or thread wrapped around core 14 and support element 28. Support element 28 is positioned within the inner perimeter 22 of core 14. Loops 26 have generally rounded tips 32 which fit within the proximal end (with respect to the surgeon) of the sheath 34 to form the suture guard 12. The rounded tips 32 reduce the likelihood that the sheath may be damaged.

FIG. 2 shows a perspective cross sectional view of a portion of core 14 including bendable elements 16 covered by fabric sheath 34. In the embodiment shown in FIG. 2, coupling member 30, such as sutures, are not used to attach bendable elements 16 to core 14. Instead, bendable elements 16 are attached to core 14 by some other means, such as through the use of an adhesive. In FIG. 2, one of the wire loops 26 is shown in an open position 36 and in a closed position 38 with dashed lines. In the closed position 38, suture guard 12 covers suture knot 20 and suture knot surface 18.

In operation, a surgeon implants and secures annuloplasty ring 10 in a patient by suturing core 14 to the tissue annulus proximate the heart valve of a patient using known surgical techniques. This produces a plurality of suture knots 20. Following attachment of prosthesis ring 10 to the patient, the surgeon actuates suture guard 12 by bending suture guard 12 toward core 14 such that suture guard 12 covers suture knots 20 and suture knot surface 18. Bendable elements 16 provide a mechanism to maintain suture guard 12 in a closed position 38 following implantation.

Figure 3A:
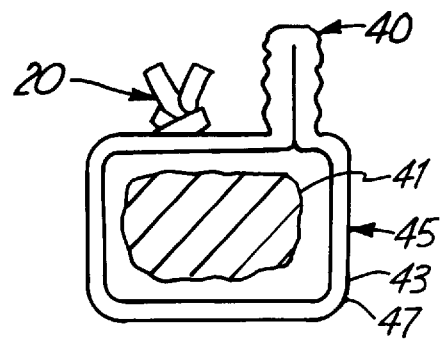
FIGS. 3A and 3B are cross-sectional views showing a suture guard in accordance with another embodiment.
Figure 3B:
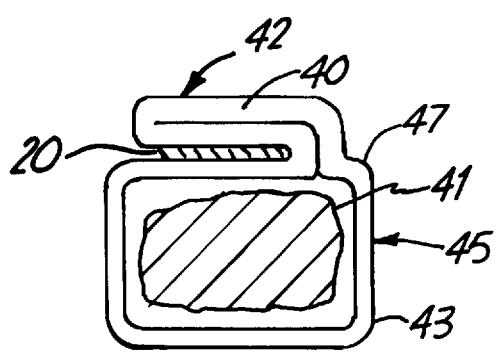

FIGS. 3A and 3B show cross-sectional views of another suture guard embodiment. In FIGS. 3A and 3B, a suture guard 40 is positioned on the outer perimeter 43 of ring 45 carried on core 41 and is shown as being integral with sheath 47. This differs from the embodiment of FIGS. 1A, 1B and 2 in which suture guard 12 is positioned on an inner perimeter. FIG. 3A shows suture guard 40 in an open position such that suture knot 20 is exposed. In FIG. 3B, suture guard 40 has been folded over to cover suture knot 20. A smaller secondary suture knot 42 may be used to maintain suture guard 40 in the closed position in FIG. 3B.

In another embodiment, a biocompatible adhesive or fibrin glue is placed between suture guard 40 of FIGS. 3A and 3B and sheath 47. This adhesive replaces secondary suture 42 and secures guard 40 in the closed position. Typically, the suture guard is formed of a compliant material, such as woven polyester or polytetrafluoroethylene (PTFE).

Another alternative method for fastening the suture guard to the annuloplasty ring is using hook and loop fasteners, commonly known as Velcro®. In this embodiment, the hook portion of the fastener is located on either the distal side of the suture guard which contacts the suture knot or the proximal side of the ring. The loop is located on the opposite mating surface from the hook. When the suture guard is maneuvered into place so the knots are covered, the hook and loop fasteners take hold and prevent the suture guard from revealing the knots and maintain the guard in the closed position. Alternative embodiments may also include securing the suture guard in position by bonding materials together, such as by ultrasonic welding.

Figure 4A:
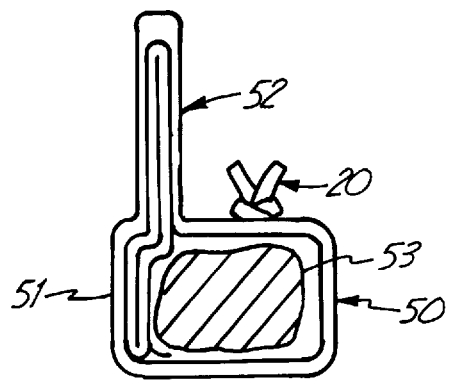
FIGS. 4A and 4B are cross-sectional views showing a suture guard in accordance with another embodiment.
Figure 4B:
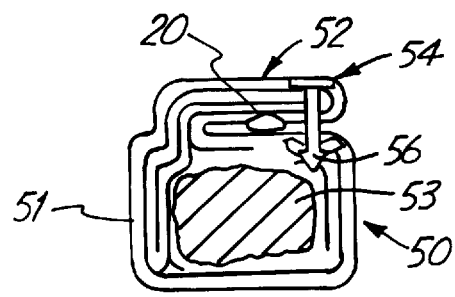

FIGS. 4A and 4B show cross-sectional views of a suture guard 52 for ring 50 in accordance with another embodiment. Suture guard 52 is formed integral with sheath 51 and is folded over as shown in FIG. 4B to cover sheath 51 and suture knot 20. Sheath 51 covers core 53. A barbed fastener 54 is placed through suture guard 52 by a surgeon and into sheath 51 as shown in FIG. 4B. Barbed fastener 54 includes a barbed point 56 which locks fastener 54 in sheath 51, thereby maintaining suture guard 52 in a closed position. Suture guard 52 may couple to an interior perimeter of ring 50 in FIGS. 4A and 4B or, in an alternative embodiment, to an exterior perimeter of ring 50.

Figure 5A:
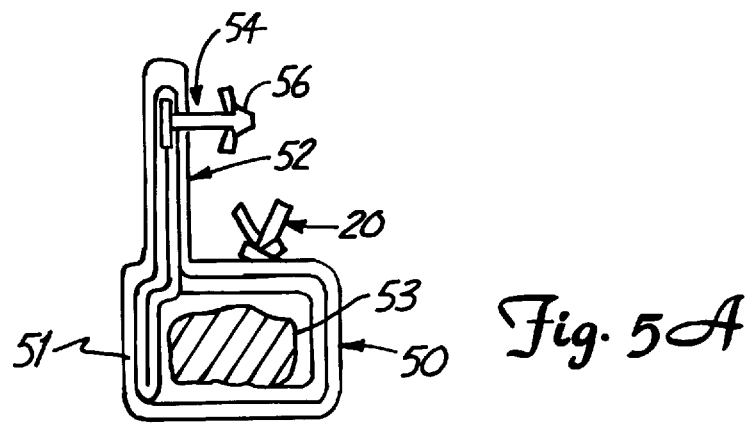
FIGS. 5A and 5B are cross-sectional views showing a suture guard in accordance with another embodiment.
Figure 5B:
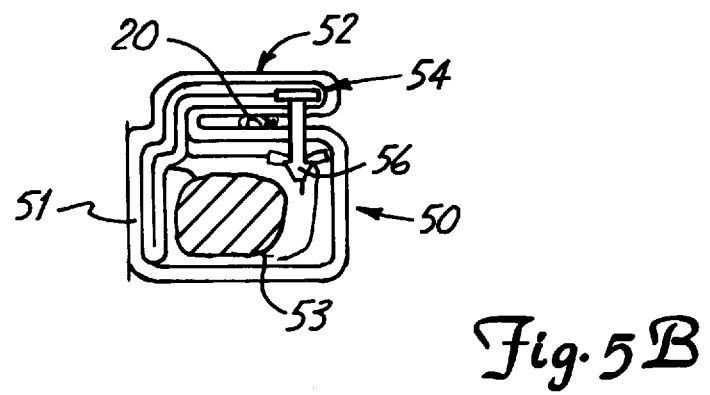

FIGS. 5A and 5B are cross-sectional views which show variations on the embodiment of FIGS. 4A and 4B. In FIGS. 5A and 5B, barbed fastener 54 is embedded in the distal end of suture guard 52. The advantage of this technique over that shown in FIGS. 4A and 4B is that closing of the suture guard 52 as shown in FIG. 5B may be faster and easier for the surgeon, and any thrombotic complications associated with additional exposed fastener material are eliminated. Additionally, the barbed fasteners 54 are integral with suture guard 52 for an added measure of safety. Barbed fasteners 54 may be constructed as independent objects or attached to a continuous flexible ring. Barbed fasteners may include staples.

One technique for maintaining the suture guard in a closed position is to spring load the suture guard. This may be particularly useful in the case of small annuloplasty rings in which it may be difficult to attach the free end of the suture guard to the ring. A spring or flexible member may be placed on the interior or exterior of the suture guard. In the relaxed position, the spring would maintain the suture guard in a closed position covering the sutures and suture knots without requiring any additional securing mechanism. The spring can be moved into a position which exposes the proximal side of the ring (i.e., an open position) allowing the ring to be sutured to the heart tissue annulus by the surgeon.

Figure 6A:
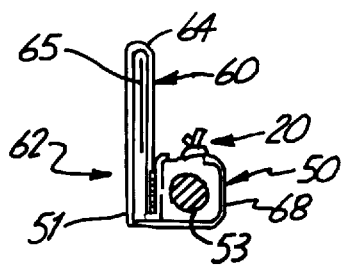
FIGS. 6A and 6B are cross-sectional views of a suture guard in accordance with another embodiment.
Figure 6B:
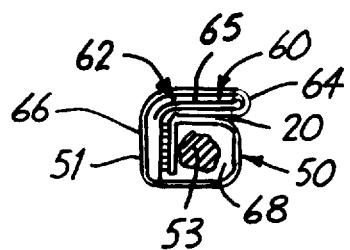
Figure 6C:
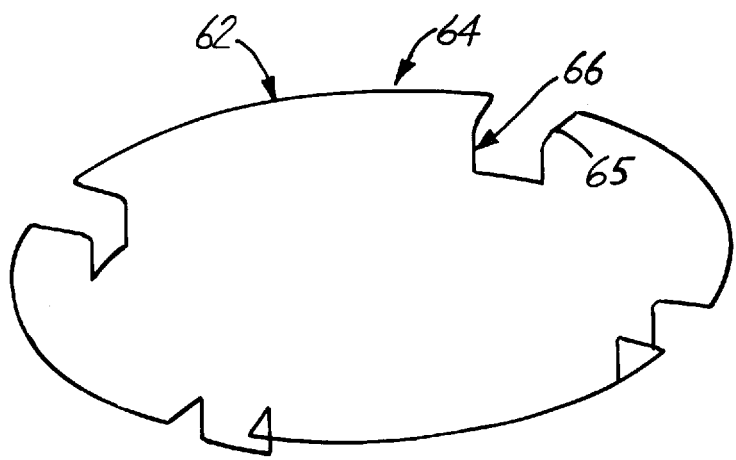
FIG. 6C is a top perspective view of a spring for use with the suture guard shown in FIGS. 6A and 6B.

FIGS. 6A and 6B show cross-sectional views of a suture guard 60 in accordance with another embodiment which utilizes a spring element 62, such as wire formed spring as shown in FIG. 6C, to maintain the suture guard 60 in a closed position. FIG. 6C is a top perspective view of spring element 62 in the closed position shown in FIG. 6B. Spring 62 includes circumferential portion 64, radial portion 65 and axial portion 66. Radial portion 65 extends into the suture guard 60 and is visible in the cross sections of FIGS. 6A and 6B. The axial portion 66 of spring 62 extends in an axial direction along ring 50 and is positioned between sheath 51 and core 53. Spring 62 is captured within suture guard 60, and is fixed to ring 50. Preferable materials for spring 62 include polymers such as acetal, or metals such as Elgiloy® (cobalt-chrome alloy) or MP35N (cobalt-nickel alloy).

Figure 7A:
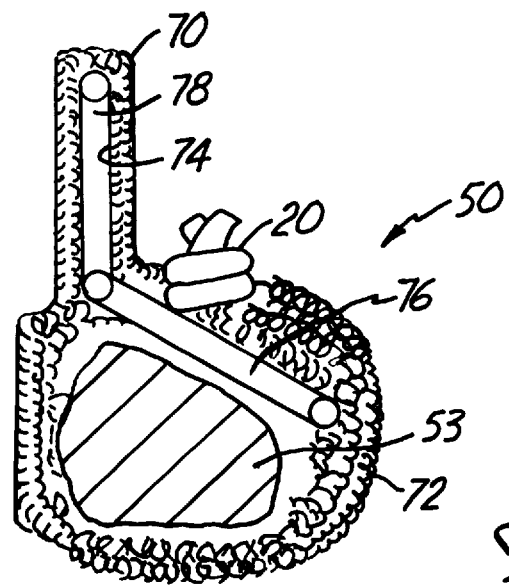
FIGS. 7A and 7B are cross-sectional views of a suture guard in accordance with another embodiment.
Figure 7B:
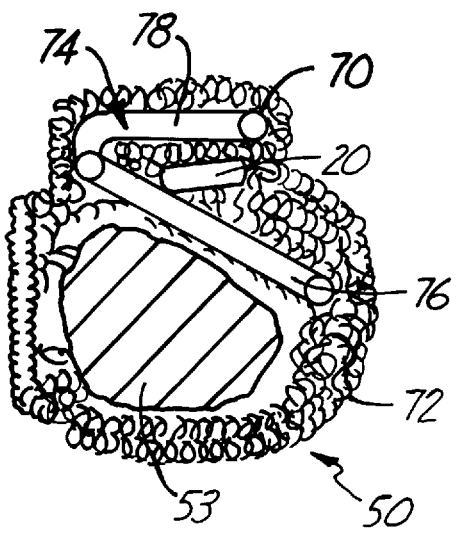

FIGS. 7A and 7B are cross-sectional views of a spring loaded suture guard 70 in accordance with another embodiment. In FIGS. 7A and 7B, suture guard 70 extends from sheath 72 proximate suture knot 20. An angled spring member 74 is carried in suture guard 70 and sheath 72. A lower portion 76 of spring member 74 is captured in sheath 72 while a movable portion 78 is provided in suture guard 70. Spring 74 is biased to the closed position shown in FIG. 7B. One advantage of this embodiment is that force from spring 74 is applied proximate both sides of suture knot 20 and thus tightly shields knot 20.

Figure 8A:
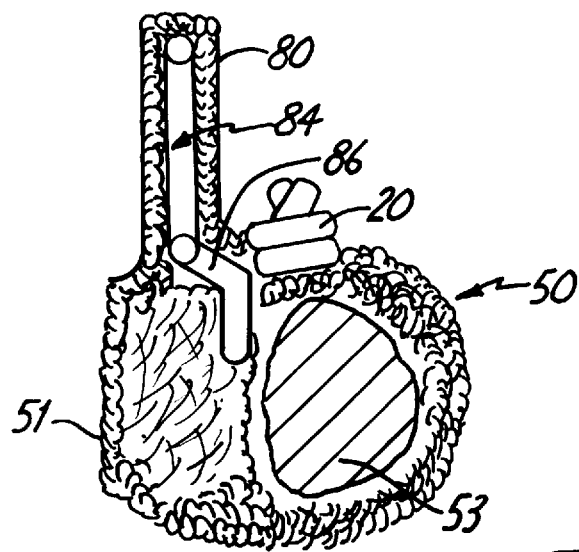
FIGS. 8A and 8B are cross-sectional views of a suture guard in accordance with another embodiment.
Figure 8B:
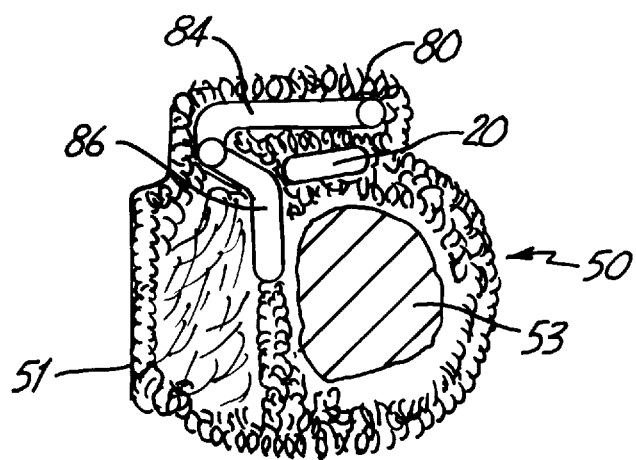

FIGS. 8A and 8B show cross-sectional views of a spring-loaded suture guard in accordance with another embodiment. Suture guard 80 extends from ring 50 proximate suture knot 20 to cover suture knot 20 and sheath 51. A spring 84, such as a wire formed spring, is carried in guard 80 and sheath 51. FIG. 8B shows guard 80 positioned over knot 20 by spring 84. Fixed end 86 of spring 84 is attached to core 53. Attachment of fixed portion 86 to core 53 may be through any appropriate technique such as biocompatible adhesive, bonding or welding.

Figure 9A:
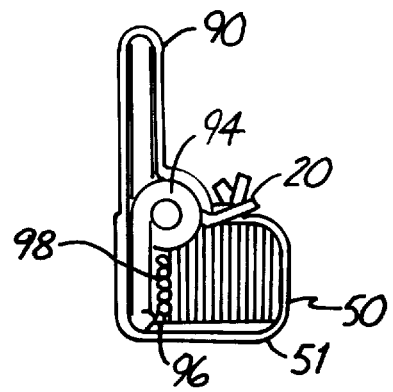
FIGS. 9A and 9B are cross-sectional views of a suture guard in accordance with another embodiment.
Figure 9B:
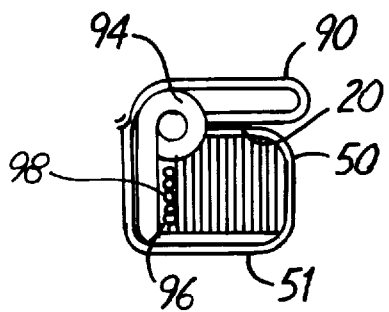

FIGS. 9A and 9B show cross-sectional views of a spring-loaded suture shield in accordance with another embodiment. Suture guard 90 extends from ring 50 proximate suture knot 20. A coiled spring 94 is carried in suture guard 90 and sheath 51, and is biased to the closed position shown in FIG. 9B. A fixed end 96 of spring 94 is secured within ring 50 by, for example, suture attachment windings 98. A coiled spring is advantageous because deflection of the spring member is less likely to cause permanent deformation from the original biased shape of the spring.

Figure 10:
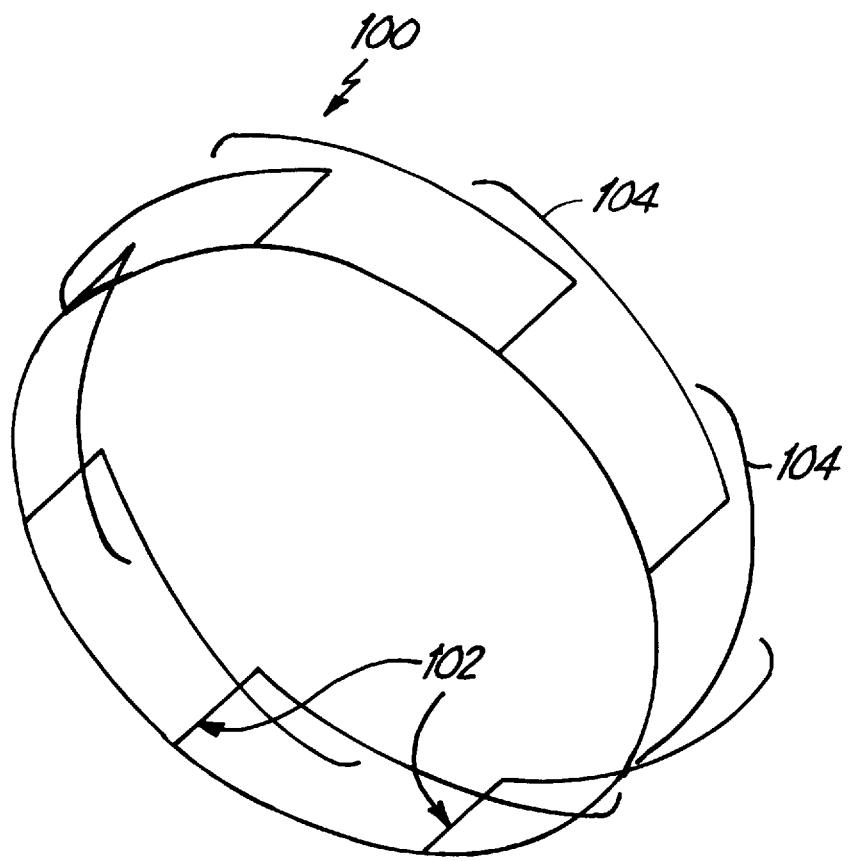
FIG. 10 is a perspective view showing a spring for retaining a suture guard in accordance with one embodiment.

FIG. 10 is an isometric view of a spring 100 for use with a suture guard in a manner similar to that shown in FIGS. 6A through 9B. Spring 100 includes axial or fixed portions 102 which carry arms 104. Arms 104 are movable between an open position (such as shown in FIG. 6A) and a closed position (such as shown in FIG. 6B) covering the suture knot 20. Attachment of spring 100 to ring 50 would occur at the fixed or axial portion 102 of spring 100.

Figure 11A:
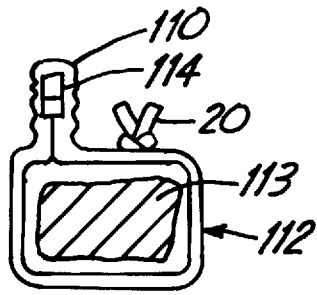
FIGS. 11A and 11B are cross-sectional views of a suture guard in accordance with another embodiment.
Figure 11B:
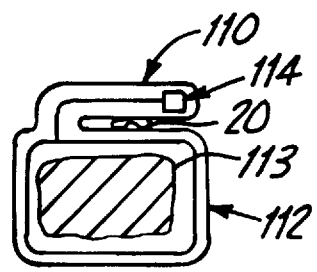

FIGS. 11A and 11B are cross-sectional views of suture guard 110 in accordance with another embodiment. Suture guard 110 extends from sheath 112 carried on core 113 and carries spring member 114 at a distal end. Spring member 114 is an annular spring extending around the outer perimeter of the annuloplasty ring. Spring member 114 is biased to a shape which has a perimeter greater than or equal to the perimeter formed by suture guard 110 in the closed position of FIG. 11B. This causes suture guard 110 to be held in the closed position of FIG. 11B, thereby covering suture knot 20.

Figure 12A:
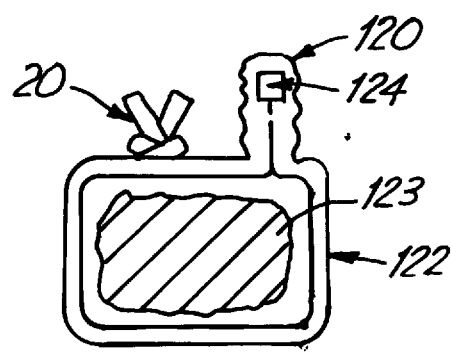
FIGS. 12A and 12B are cross-sectional views of a suture guard in accordance with another embodiment.
Figure 12B:
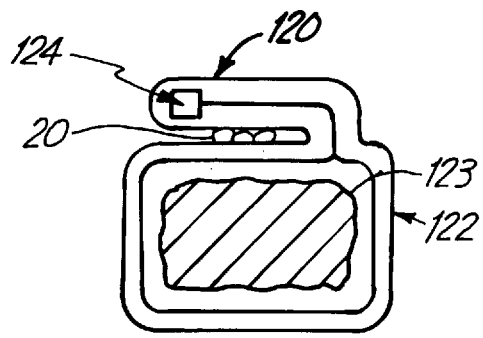

FIGS. 12A and 12B are cross-sectional views of suture guard 120 in accordance with another embodiment similar to the embodiment of FIGS. 11A and 11B. Suture guard 120 extends from the outer perimeter of the annuloplasty ring and is carried in sheath 122 coupled to core 123. The proximal end of suture guard 120 carries annular spring 124. Annular spring 124 is biased to a shape which is sized smaller than or equal to the outer perimeter of the annuloplasty ring. This causes spring 124 to maintain suture guard 120 in the closed position shown in FIG. 12B, thereby covering suture knot 20.

Figure 13A:
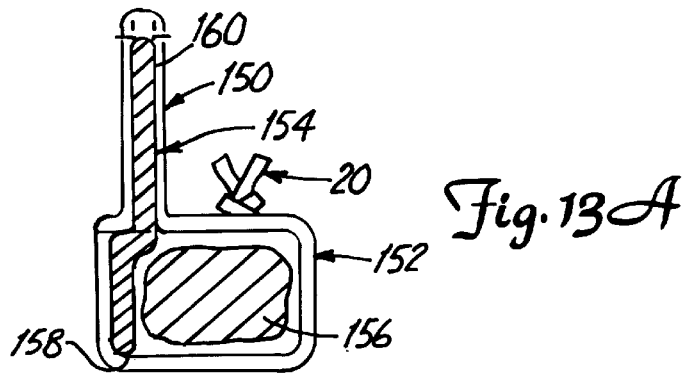
FIGS. 13A and 13B are cross-sectional views of a suture guard in accordance with another embodiment.
Figure 13B:
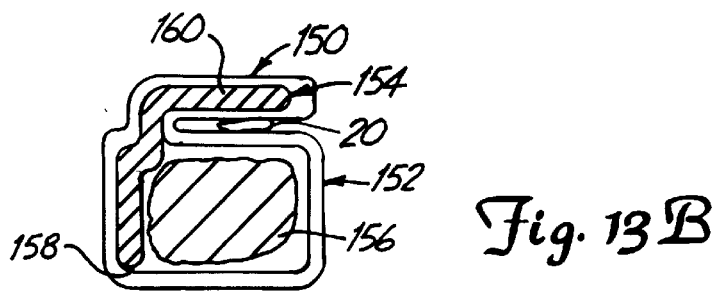
Figure 13C:
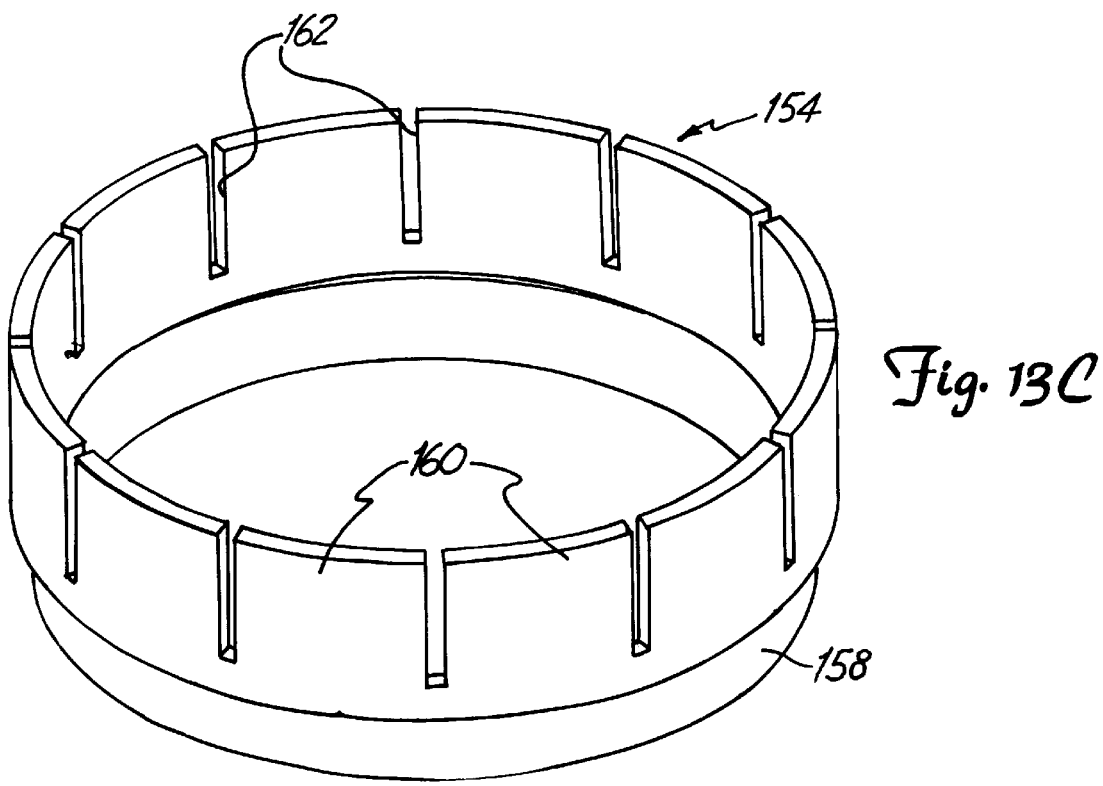
FIG. 13C is a top perspective view of a member for maintaining a suture guard in a closed position in accordance with the invention.

FIGS. 13A and 13B show cross-sectional views of suture guard 150 in accordance with another embodiment. Suture guard 150 includes spring insert 154 which extends from core 156 and is covered by sheath 152. Insert 154 is secured to core 156 using any appropriate means, such as a biocompatible adhesive. FIG. 13C is a top perspective view of insert 154. Insert 154 includes fixed portion 158 and movable portions 160 which is used to cover a portion of sheath 152 and suture knot 20. Movable portions 160 are separated by gaps 162 which allow movable portions 160 to be deflected radially outward. Insert 154 is biased to the closed position shown in FIG. 13B such that suture guard 150 covers suture knot 20.

Attachment of the fixed portion of the springs set forth herein may be through any appropriate technique. For example, suture windings, retainer rings, stiffening rings or stents may be employed. The members are preferably manufactured from biocompatible materials such as metals or polymers, for example.

In the embodiments of FIGS. 6A through 10 and 13A through 13B, the spring member can be replaced with a malleable material. The initial shape of the material is in the open position. After a surgeon has fixed the annuloplasty ring to the tissue annulus, the surgeon pushes or forms the malleable material over the suture and suture knots. This may be accomplished by either using the surgeon's finger or a tool. Suitable examples of malleable materials include polymers or metals such as tantalum or titanium.

The embodiments set forth in FIGS. 3 through 13 may be manufactured from materials which are temperature responsive. In these materials, a change in temperature causes the suture guard to move to the closed position. There are numerous materials which exhibit this shape memory characteristic, such as shape memory metals or polymers. For example, NiTinol® (available from 3M Corporation of Minnesota) and other heat polymer materials such as heat-shrink polyester may be employed. NiTinol® is an intermetallic compound comprising a nickel titanium alloy which can be deformed and which will remain in the deformed shape until heat is applied. Materials having similar characteristics may also be used. In the present invention, the material would be deformed such that the suture guard is in the open position. After suturing has been completed, the surgeon applies heat to activate the material causing the guard to assume its closed position. Application of heat by warmed cardioplegia solution, for example, can cause the material to deform to its original heat-set condition. This provides a quick and easy technique for the surgeon to cover the suture and suture knots. Thermally activated material, such as a polyester heat shrink material which contracts radially inward to a closed position may also be employed. For example, this could be used in the embodiment shown in FIGS. 12A and 12B.

Figure 14B:
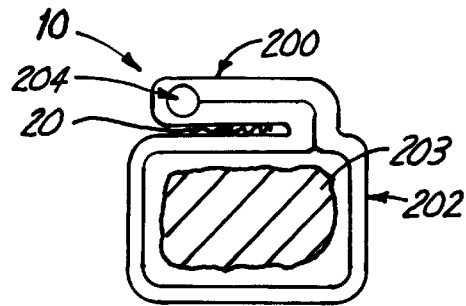
FIGS. 14A and 14B are cross-sectional views of a suture guard using a drawstring technique.
Figure 14A:
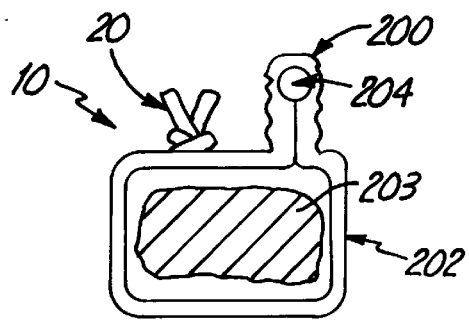
Figure 14C:
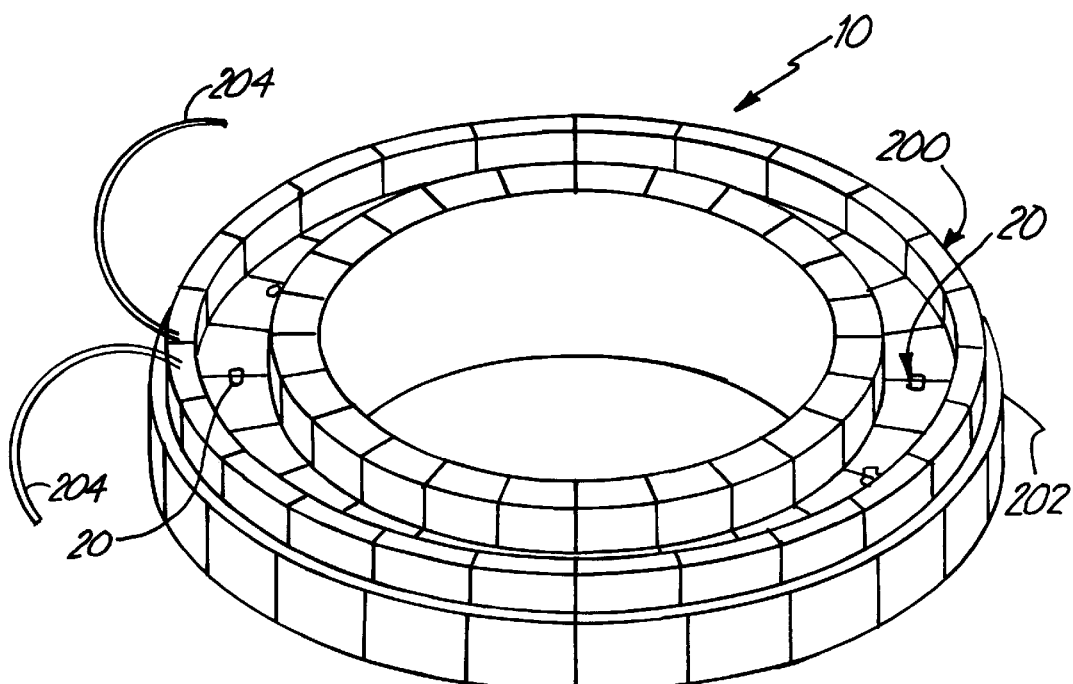
FIG. 14C is a top plan view of the suture guard of FIGS. 14A and 14B in an open position.
Figure 14D:
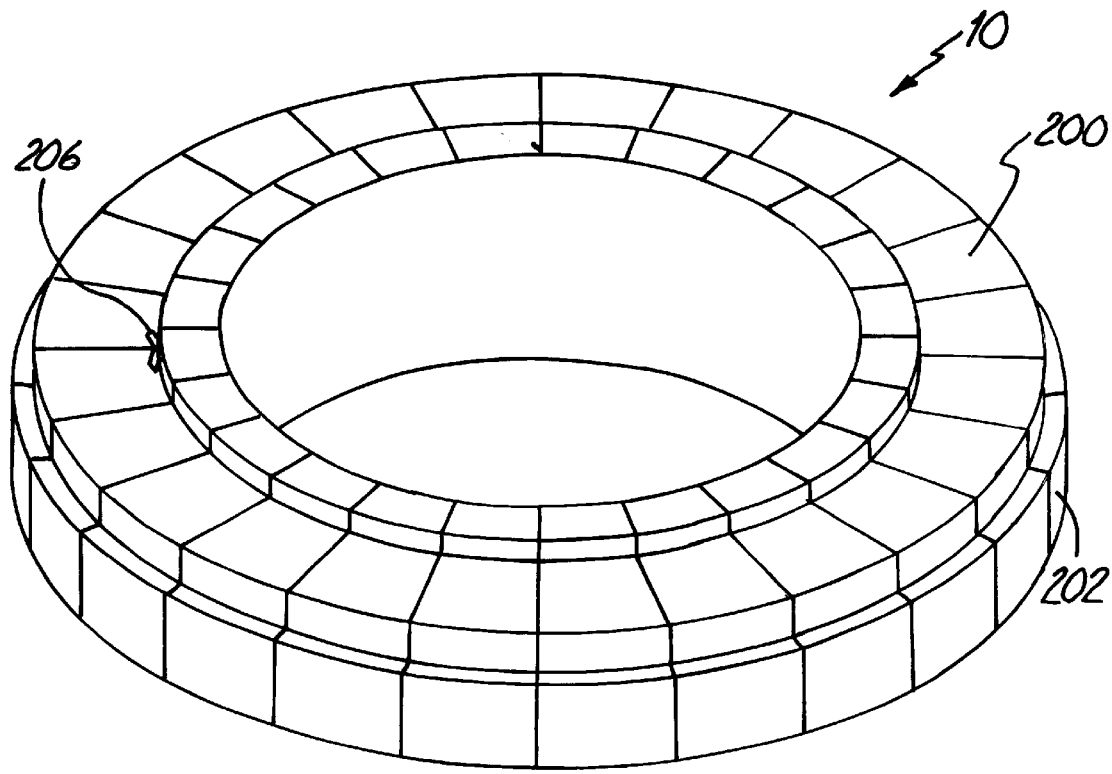
FIG. 14D is a top plan view of a suture guard of FIGS. 14A and 14B in a closed position.

Another technique for restraining the suture guard is through the use of drawstring sutures. Using this technique, sutures are placed within the proximal end, with respect to the surgeon, of the suture guard. FIGS. 14A through 14D show such a drawstring technique. FIGS. 14A and 14B are cross-sectional views showing suture guard 200 extending from the outer perimeter of annuloplasty ring 10. A drawstring 204 extends through the proximal end of suture guard 200 and is carried in sheath 202 which covers core 203. As shown in FIG. 14B, in the closed position, suture guard 200 covers suture knot 20. FIG. 14C is a top perspective view of suture guard 200 in the open position, as depicted in FIG. 14A. In this position, ring 10 is exposed, allowing the surgeon to form suture knots 20. After suturing has been completed, the surgeon pulls drawstring 204 to move suture guard 200 to the position shown in FIG. 14D. In FIG. 14D, drawstring 204 has been tightened causing guard 200 to be pulled inward, thereby covering suture knots 20. Drawstring knot 206 is formed from drawstring 204 and may be placed under suture guard 200 thereby covering drawstring knot 206.

Figure 15A:
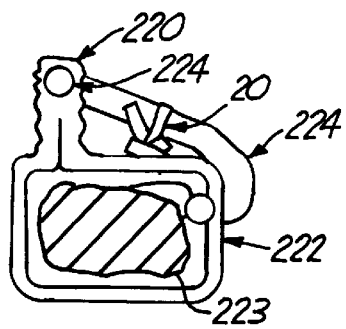
FIGS. 15A and 15B are cross-sectional views of a suture guard using a drawstring technique.
Figure 15B:
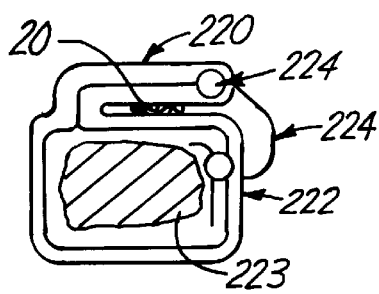
Figure 15D:
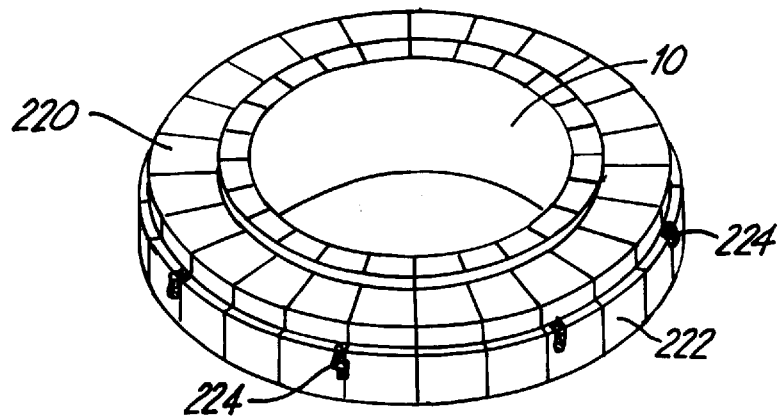
FIG. 15D is a top plan view of a suture guard of FIGS. 15A and 15B in a closed position.
Figure 15C:
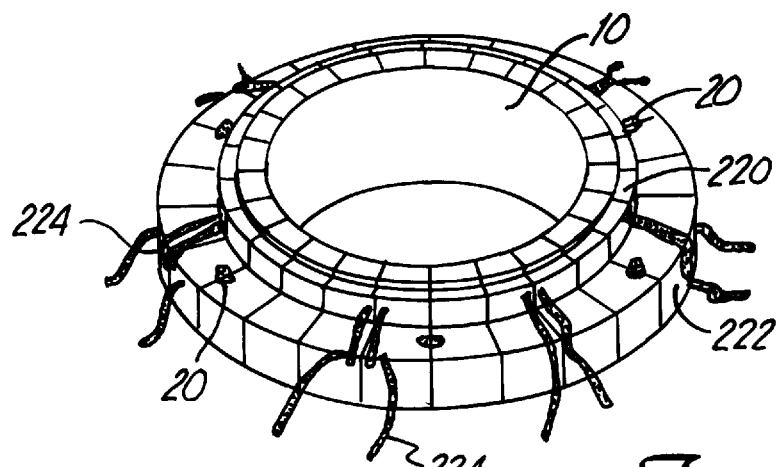
FIG. 15C is a top plan view of the suture guard of FIGS. 15A and 15B in an open position.

FIGS. 15A through 15D show another technique using drawstrings to implement a suture guard. FIGS. 15A and 15B are cross-sectional views showing suture guard 220 extending from the inner perimeter of ring 10. Drawstrings 224 are carried through the proximal end of suture guard 220 and extend into sheath 222. As shown in FIG. 15B, drawstrings 224 are tightened, thereby closing suture guard 220. FIG. 15C is a top perspective view showing ring 10 having suture guard 220 in an open position. As shown in FIG. 15C, drawstrings 224 loop through suture guard 220 and sheath 222. As the surgeon pulls drawstrings 224, suture guard 220 is moved to the closed position as shown in the perspective view of FIG. 15D. After cinching drawstrings 224, the drawstrings are knotted, thereby securing suture guard 220 in the closed position as shown in FIG. 15D. The drawstring embodiments are advantageous because the suturing techniques are familiar and expected by surgeons.

In another embodiment, magnets may be employed in the sheath or core and suture guard to maintain the suture guard in a closed position. The suture guard set forth herein is formed of biocompatible materials.

Figure 16:
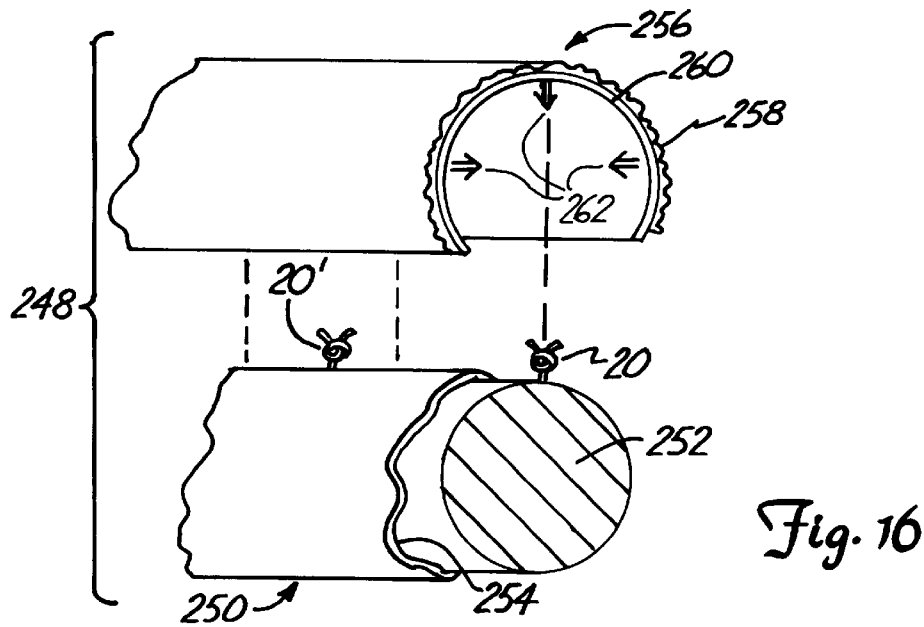
FIG. 16 is a cut-away cross sectional exploded view showing a separate suture guard in accordance with another embodiment.

FIG. 16 is a cross sectional view of an annuloplasty ring assembly 248 in accordance with another embodiment. In assembly 248, annuloplasty ring 250 is shown and includes core 252 and sheath 254 which carry suture knots 20. A suture guard 256 is shown adjacent ring 250 and is formed from U-shaped cover 258 and attachment element 260. Suture guard 256 may extend around the entire circumference of ring 250 or may be a small clamp which only partially covers ring 250. Attachment element 260 elastically deforms to apply clamping force to more securely attach guard 256 to ring 250. In a variation of this embodiment, barbs 262 are protruding inwardly from guard 256 and are used to fasten guard 256 to sheath 254. In a variation on this embodiment, an attachment element 260 is plastically deformed to clamp suture guard 256 to ring 250.

The suture guard 256 may be attached to ring 250 by any number of methods described above, such as adhesives or hook and loop fasteners. Additionally, the shape of suture guard 256 may vary depending on the shape of the core or the degree of coverage of the ring 250 desired by the surgeon. The cover 258 may be attached using an element which is plastically formed such as a staple, i.e. malleable, or elastically formed, such as a spring, around ring 250.

Figure 17:
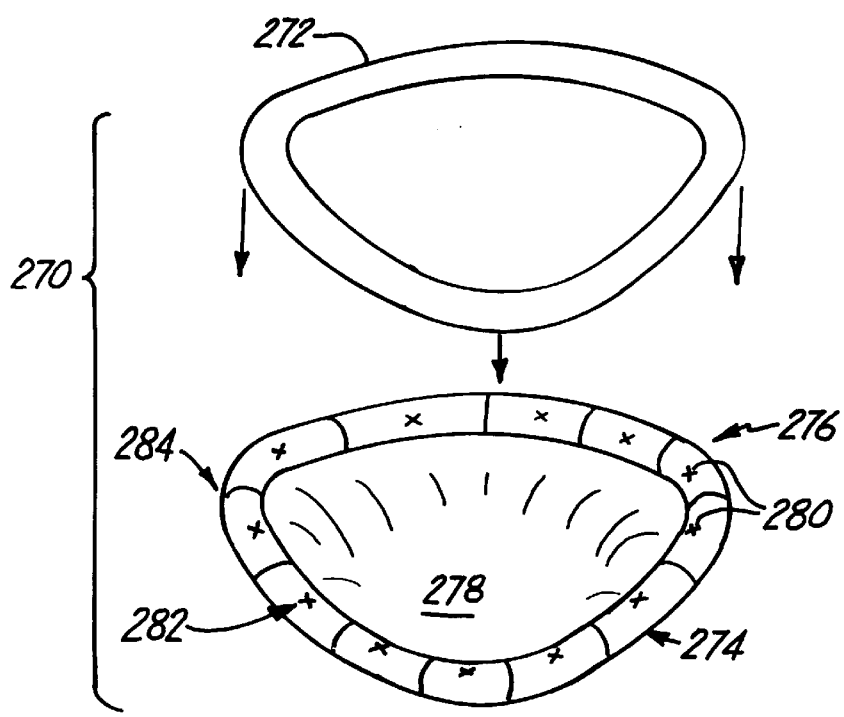
FIG. 17 is an exploded view showing an annuloplasty ring and band for providing a suture guard in accordance with another embodiment.

FIG. 17 is an exploded perspective view of an annuloplasty ring device 270 including annuloplasty ring 272 and band 274 which provide a suture guard in accordance with another embodiment. Band 274 is preferably made of a biocompatible fabric and is shown in FIG. 17 sutured to the natural tissue annulus 276 of a patient proximate the mitral valve 278 using sutures 280 which are knotted at suture knots 282. Band 274 includes a plurality of U-shaped clips 284 carried thereon. Clips 284 may be metallic or a polymer. In the embodiment of FIG. 17, a surgeon sutures band 274 to annulus 276. Annuloplasty ring 272 is then snapped in place over band 274 covering suture knots 282 and is held in place by U-shaped clips 284. Other appropriate attachment techniques such as barbs, adhesives, hook and loop fasteners, etc. may also be used.

Figure 18:
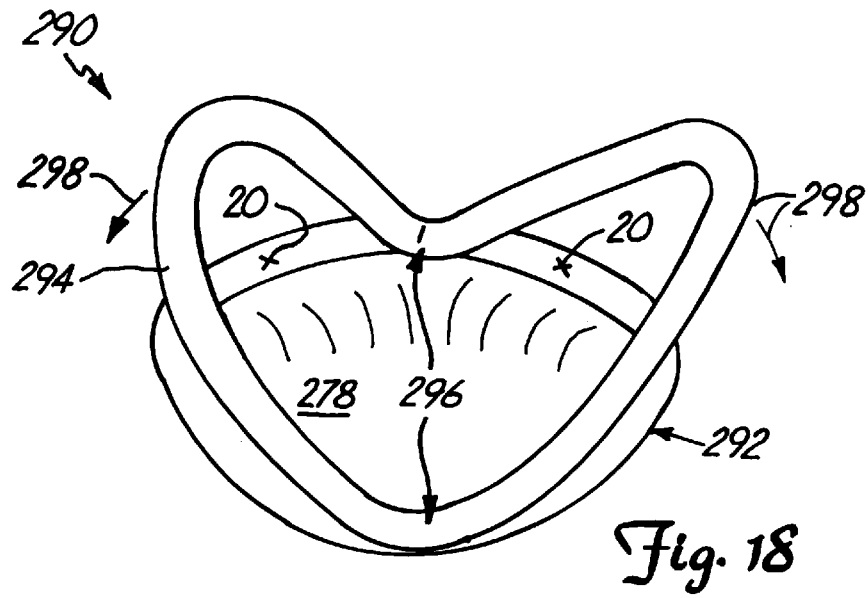
FIG. 18 is a perspective view of a hinged suture guard.

FIG. 18 is a perspective view of an annuloplasty ring device 290 in accordance with another embodiment which includes annuloplasty ring 292 and suture guard 294. Ring 292 is shown attached to the tissue annulus proximate mitral valve 278 using sutures which have suture knots 20. Suture guard 294 is attached to ring 292 at pivots 296. After suturing ring 292 to the tissue annulus, suture guard 294 is moved in the direction shown by arrows 298 about pivots 296 such that guard 294 covers ring 292. Guard 294 may be made of a biocompatible fabric material and may be held in place over suture knots 20 by any means. Variations on this embodiment include using a malleable material carried in a fabric suture guard 294 which may be bent into shape and using a malleable material without any covering. Additionally, other types of attachment techniques may be used. Pivots 296 may be attached to ring 292 using sutures or any other appropriate technique.

Figure 19A:
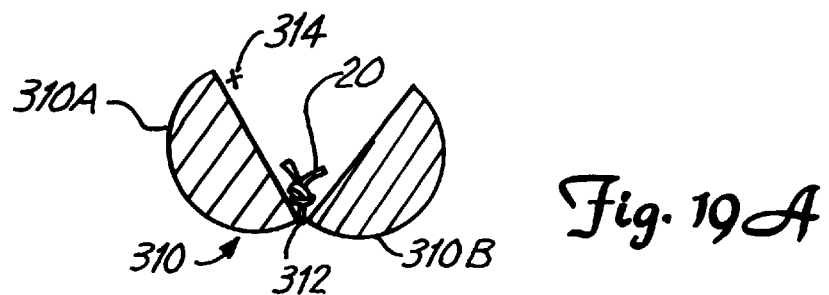
FIG. 19A is a cross sectional view of a ring prosthesis in which a suture knot is protected within the ring prosthesis.
Figure 19B:
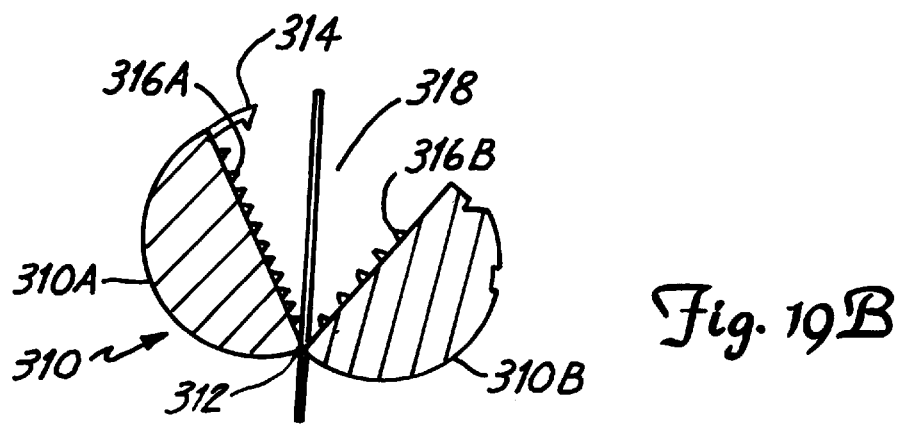
FIG. 19B is a cross sectional view of a ring prosthesis which clamps a suture in accordance with one embodiment of the present invention.

FIGS. 19A and 19B are cross sectional views of two additional embodiments which provide a suture guard to an annuloplasty ring. In FIG. 19A, annuloplasty prosthesis ring 310 is formed of a core in two halves (or portions) 310A and 310B joined at joint 312. Annuloplasty ring 310 is implanted in the patient with halves 310A and 310B in the open position shown in FIG. 19A. The suture is run through ring 310 proximate joint 312 and knotted to form suture knots 20. After the annuloplasty ring 310 is implanted, halves 310A and 310B are squeezed together such that barb 314 attaches half 310A to half 310B. In this closed position, suture knot 20 is protected and shielded between halves 310A and 310B.

The embodiment of FIG. 19B is similar to the embodiment of FIG. 19A except that halves 310A and 310B include gripping surfaces 316A and 316B, respectively. A suture 318 which is used to attach ring 310 to the tissue of the patient is placed through a small opening proximate joint 312. The two halves 310A and 310B are squeezed together such that suture 318 is locked between surfaces 316A and 316B. The two halves 310A and 310B are held together by barb 314 such that suture 318 is secured between halves 310A and 310B. In this embodiment, suture 318 need not be knotted. Other attachment techniques may also be employed such as mechanical latches or biocompatible adhesives.

While many of these embodiments show the suture guard as being integral with the annuloplasty ring, it is within the contemplation of this invention that the suture guard can also be a separate entity which can be selectively attached to the annuloplasty ring. In addition, the suture guard and/or core may optionally not be sheathed. Further, a pharmaceutical or a bioreactive chemical coating or treatment may be applied to the suture guard, such as a tissue growth enhancer or an anti-bacterial coating. This is advantageous because the suture guard covers the sutures and suture knot which may not be treated with the coating. Thus, the patient is not exposed to uncoated surfaces of the suture material. Furthermore, in the present invention the suture knot is covered which may reduce the likelihood of thrombosis.

The suture guard can be used with any attachment technique such as suturing or stapling. Suturing techniques include everted mattress sutures, non-everting mattress sutures, figure of eight sutures or continuous sutures. The suture guard may be formed integral with the ring assembly. The suture guard is easily manufactured at a low cost and can be easily used by surgeons with their preferred attachment methods. The suture guard can be adapted and implemented with most existing annuloplasty ring prostheses. Some of the embodiments are self-actuated and will engage the suture knot upon release by the surgeon. The suture guard tends to be flexible because it lies on the attachment portion of the ring and therefore has the ability to conform to the irregularities. The current preferred method of attaching valve repair devices such as annuloplasty rings to the native heart tissue is with sutures. The sutures are placed through the native tissue and fabric of the annuloplasty ring. The sutures are then knotted to secure the ring to the tissue. Some of the remaining length of suture is then trimmed leaving a suture stub end. It is perceived that the knots and remaining suture ends are a source of thrombosis and embolic complications following implantation of annuloplasty rings and that if the suture knot ends are too long they may disrupt the leaflet function of the valve. One aspect of this invention is to allow the surgeon to implant the ring using any preferred method and then cover the attachment mechanism after the ring has been attached to the native valve. However, the present invention may be employed with any attachment mechanism. For example, the attachment mechanism shown in the figures and referred to as sutures may be any attachment mechanism such as staples or clips and attached adjacent on attachment surface.

Although the present invention has been described with reference to preferred embodiments, workers skilled in the art will recognize that changes may be made in form and detail without departing from the spirit and scope of the invention. Typical materials are described in many of the preferred embodiments. However, applicable materials shall not be limited to those mentioned. Applicable materials include any biocompatible polymer, metal or other material that provide the desired characteristics described for the embodiments.

What is claimed is:

1. An anniloplasty ring assembly for implantation proximate a heart valve tissue annulus, comprising:

an annuloplasty ring having a size and shape to generally conform to the heart valve annulus;

an attachment mechanism surface on the annuloplasty ring assembly;

an attachment mechanism wherein the attachment mechanism is positioned adjacent the attachment mechanism surface of the annuloplasty ring assembly; and an attachment mechanism guard adapted to selectively couple to the annuloplasty ring assembly and moveable between a mechanism exposed position in which the attachment mechanism surface and the attachment mechanism are exposed and a mechanism covered position covering the attachment mechanism surface and the attachment mechanism carried on the attachment surface.

2. The annuloplasty ring assembly of claim 1 including an adhesive securing the attachment mechanism guard in the mechanism covered position.

3. The annuloplasty ring assembly of claim 1 including a barb coupled to the attachment mechanism guard which secures the attachment mechanism guard to the annuloplasty ring in the closed position.

4. The annuloplasty ring assembly of claim 1 wherein the attachment mechanism guard includes a bendable element.

5. The annuloplasty ring assembly of claim 1 wherein the attachment mechanism guard attaches to the annuloplasty ring proximate an inner perimeter of the annuloplasty ring and extends in a generally radially outward direction when in the mechanism covered position.

6. The annuloplasty ring assembly of claim 1 wherein the attachment mechanism guard attaches to the annuloplasty ring proximate an outer perimeter of the annuloplasty ring and extends in a generally radially inward direction when in the mechanism covered position.

7. The annuloplasty ring assembly of claim 1 further comprising a spring member coupled to the attachment mechanism guard which maintains the attachment mechanism guard in the mechanism covered position.

8. The annuloplasty ring assembly of claim 7 wherein the spring member is coupled to the annuloplasty ring.

9. The annuloplasty ring assembly of claim 7 wherein the spring member comprises a coil spring.

10. The annuloplasty ring assembly of claim 7 wherein the spring member comprises an annular spring.

11. The annuloplasty ring assembly of claim 1 further comprising a magnet positioned to maintain the attachment mechanism guard in the mechanism covered position.

12. The annuloplasty ring assembly of claim 1 further comprising a drawstring carried in the attachment mechanism guard to maintain the attachment mechanism guard in the mechanism covered position when the drawstring is cinched.

13. The annuloplasty ring assembly of claim 1 wherein the attachment mechanism guard comprises a bendable element covered by a sheath.

14. The annuloplasty ring assembly of claim 13 wherein the bendable element forms a plurality of curved loops.

15. The annuloplasty ring assembly of claim 13 wherein the annuloplasty ring includes a core and the bendable element is wrapped around the core.

16. The annuloplasty ring assembly of claim 1 wherein the annuloplasty ring includes a core and a sheath covering the core.

17. The annuloplasty ring assembly of claim 16 wherein the sheath extends from the core and forms the attachment mechanism guard.

18. The annuloplasty ring assembly of claim 1 wherein the attachment mechanism guard includes a shape memory metal.

19. The annuloplasty ring assembly of claim 1 wherein the attachment mechanism guard is heat actuated.

20. The annuloplasty ring assembly of claim 1 wherein the attachment mechanism guard is separated from the annuloplasty ring when in the mechanism exposed position.

21. The annuloplasty ring assembly of claim 1 wherein the attachment mechanism guard couples to the annuloplasty ring at a pivot and the attachment mechanism guard moves about the pivot between the mechanism exposed position and the mechanism covered position.

22. The annuloplasty ring assembly of claim 1 wherein the attachment mechanism comprises a suture and the attachment surface comprises a suture knot surface.

23. The annuloplasty ring assembly of claim 1 wherein the attachment mechanism comprises a staple and the attachment surface comprises a staple surface.

* * * * *